(12) United States Patent
Reynard

(10) Patent No.: US 8,496,583 B1
(45) Date of Patent: Jul. 30, 2013

(54) PUPIL DILATION SYSTEM

(71) Applicant: Michael Reynard, Santa Monica, CA (US)

(72) Inventor: Michael Reynard, Santa Monica, CA (US)

(*) Notice: Subject to any disclaimer, the term of this patent is extended or adjusted under 35 U.S.C. 154(b) by 0 days.

(21) Appl. No.: 13/668,229

(22) Filed: Nov. 3, 2012

(51) Int. Cl.
*A61B 1/32* (2006.01)

(52) U.S. Cl.
USPC .......................... 600/236; 600/235

(58) Field of Classification Search
USPC ................ 600/201–246
See application file for complete search history.

(56) References Cited

U.S. PATENT DOCUMENTS

| | | | |
|---|---|---|---|
| 4,257,406 A | 3/1981 | Schenk | |
| 4,387,706 A | 6/1983 | Glass | |
| 4,782,820 A | 11/1988 | Woods | |
| 4,991,567 A | 2/1991 | McCuen, II et al. | |
| 5,163,419 A | 11/1992 | Goldman | |
| 5,267,553 A | 12/1993 | Graether | |
| 5,318,011 A | 6/1994 | Federman et al. | |
| 5,322,054 A | 6/1994 | Graether | |
| 5,374,272 A | 12/1994 | Arpa et al. | |
| 5,427,088 A | 6/1995 | Graether | |
| 5,607,446 A | 3/1997 | Beehler et al. | |
| 5,634,884 A | 6/1997 | Graether | |
| 6,068,643 A | 5/2000 | Milverton | |
| 6,428,501 B1 | 8/2002 | Reynard | |
| 6,514,515 B1 | 2/2003 | Williams | |
| 6,620,098 B1* | 9/2003 | Milverton | 600/236 |
| 6,648,819 B2 | 11/2003 | Lee | |
| 6,966,913 B2 | 11/2005 | Israel | |
| 7,648,713 B2 | 1/2010 | Sawhney | |
| 2008/0243139 A1* | 10/2008 | Dusek | 606/107 |
| 2008/0269888 A1 | 10/2008 | Malyugin | |

OTHER PUBLICATIONS http:/lwww.fci-ophthalmics.com/cataract, 2013.
Injector system designed for use with pupil expansion device, Ophthalmology Times, Oct. 15, 2003.
Boris Malyugin, Malyugin Ring for Small Pupil Phaco Cases, Cataract & Refractive Surgery Today, Mar. 2008.
http://www.amo-inc.com/products/cataract/support-systems/stabileyes-capsular-tension-ring, 2013.
http://www.milvella.com/perfectpupil.html, 2008.
Barbara Boughton, New Pupil Expansion Ring for Floppy Iris, EyeNet Magazine, 2008.
Leonid Skorin, Jr., How to Avoid Intraoperative Floppy Iris Syndrome, Review of Optometry, 2010.

* cited by examiner

*Primary Examiner* — Eduardo C Robert
*Assistant Examiner* — Christina Negrellirodriguez
(74) *Attorney, Agent, or Firm* — Ash Tankha; Lipton, Weinberger & Husick

(57) ABSTRACT

A pupil dilation system including a generally circular deformable and discontinuous ring member is provided. The ring member expands circumferentially and applies an expansile force substantially uniformly around a pupillary margin of a pupil for dilating the pupil along an entirety of a circumference of the ring member. The ring member in an uncoiled configuration allows insertion of the ring member through a single incision in the eye and unfolds into a coiled configuration. A circumferential groove defined on an outer surface of the ring member allows continuous contact with the pupillary margin along the circumference of the ring member. One or more connector members are positioned on the circumference of the ring member for engaging with a surgical manipulating element that allows movement and manipulation of the ring member. The ring member is composed of a thermoplastic material or a bioabsorbable material that naturally dissolves within the eye.

43 Claims, 13 Drawing Sheets

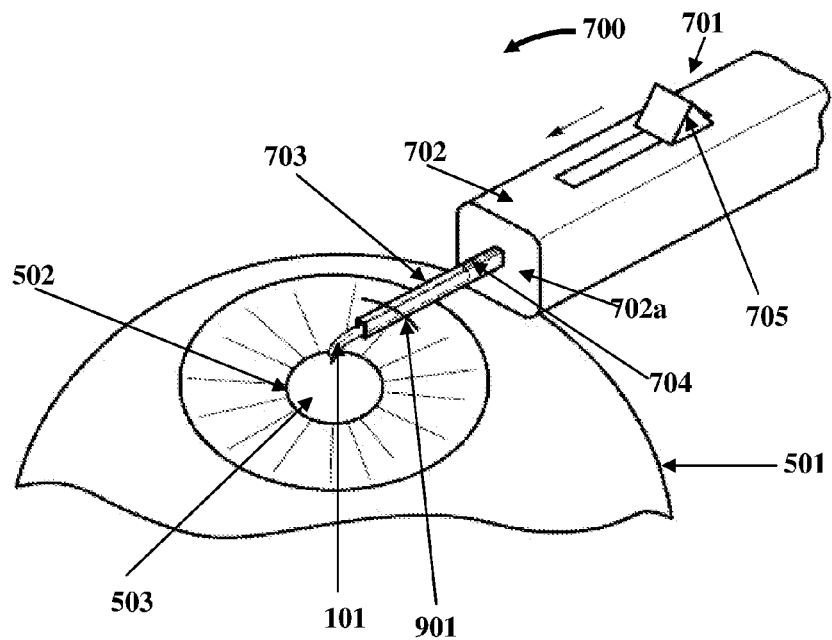
FIG. 9A
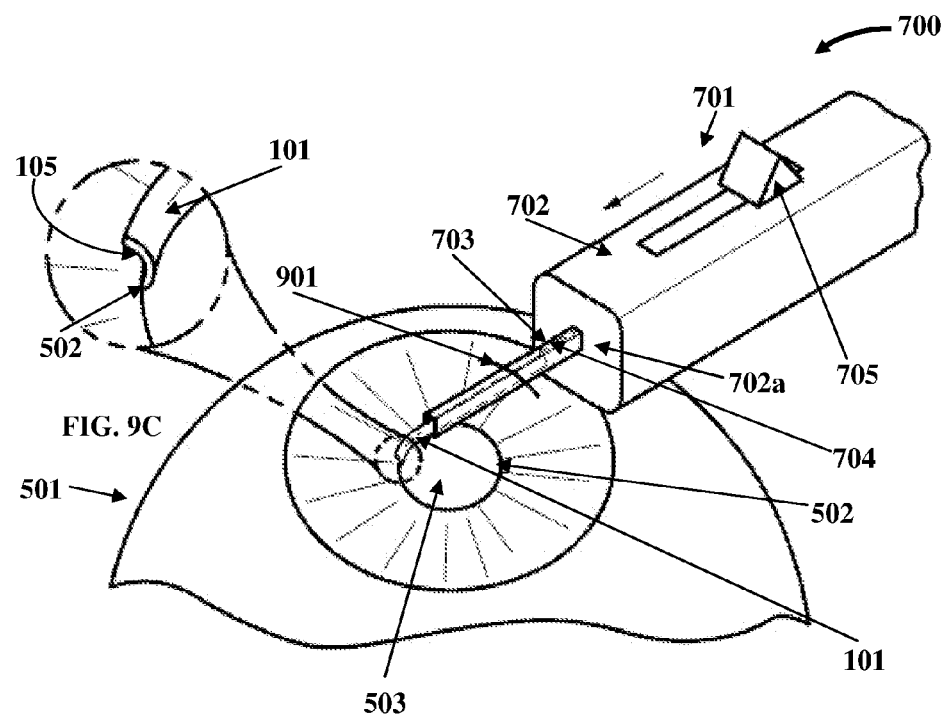
FIG. 9C
FIG. 9B

PUPIL DILATION SYSTEM

BACKGROUND

A variety of ophthalmic surgical procedures require dilation of a pupil of an eye. A full dilation of the pupil provides adequate visualization of ocular structures behind the iris of the eye and facilitates surgery of the lens, vitreous, and retina of the eye. Insufficient dilation of the pupil increases the difficulty in performing ophthalmic surgery. A patient with a small pupil poses a challenge to the surgeon during an eye surgery. A problem that is often encountered is that the diameter of the pupil remains small despite the use of eye drops to dilate the pupil. Atrophy of the pupil dilating muscle or pharmacologic blockage of the pupil dilating muscle from a variety of medications can prevent adequate enlargement of the pupil for eye surgery.

Conventional devices for enlarging the pupil by mechanical means are cumbersome to use, time consuming, and require a high level of skill by a surgeon. Moreover, conventional devices such as iris hooks require multiple incisions to be made in the eye for each hook to retract the pupil in various quadrants. Devices that expand the pupil by retracting the iris at focal points of contact with the margin of the pupil can produce excessive stretching of the iris. Focal points of stretching changes the natural shape of the pupil from a round configuration to a squared configuration. These focal stress points can result in permanent deformities in the shape of the pupil, tears of the pupillary sphincter, bleeding, and/or damage to the iris. Tears of the pupil and damage to the iris can also cause a tonic anisocoria. Moreover, disruption of delicate capillaries at the pupillary margin and the iris may also result in hyphema with elevated intraocular pressure.

Furthermore, conventional pupil expansion devices with sharp edges may damage the iris. Damage from the sharp edges of conventional sharp-edged pupil expansion devices may cause excessive post-operative inflammation and scar tissue. Moreover, complications may ensue from surgical manipulation of a conventional pupil expansion device during removal of the pupil expansion device from the eye. For example, removal of a conventional pupil expansion device can disrupt zonular fibers that stabilize a lens capsule, or cause tears of the pupillary margin that result in a distorted shape of the pupil. Surgical manipulation to remove the pupil expansion device may also disrupt the position of an intraocular lens implant.

Conventional pupil expansion devices are generally bulky and cumbersome to use. These devices are generally difficult to insert, manipulate, and remove through a small incision in the eye. For example, pupil expansion devices that are not foldable and that do not have a coiled structure cannot be easily inserted through a small incision in the eye. Pupil expansion devices that have extensions are particularly difficult to utilize during eye surgery. Moreover, conventional devices for pupillary enlargement are unstable when positioned at the pupillary margin and tend to dislodge during eye surgery. Therefore, there is a need for a pupil expansion device that is structurally simple, remains stable at the pupillary margin during eye surgery, applies a uniform expansile force around the circumference of the pupil to avoid focal stress points, and allows insertion through a small incision.

Hence, there is a long felt but unresolved need for a non-bulky, easy to use pupil dilator and a safe and stable method of pupil dilation that dilates a pupil of an eye along the circumference of the pupil by application of a substantially uniform expansile force. Moreover, there is a need for a pupil dilator that has a configuration that retains the original shape of the pupil and precludes damage to the iris and the pupil during pupil dilation. Furthermore, there is a need for a pupil dilator that can be retained in the eye after surgery to avoid complications associated with removal of the pupil dilator.

SUMMARY OF THE INVENTION

This summary is provided to introduce a selection of concepts in a simplified form that are further described in the detailed description of the invention. This summary is not intended to identify key or essential inventive concepts of the claimed subject matter, nor is it intended for determining the scope of the claimed subject matter.

The pupil dilation system and method disclosed herein address the above stated needs for dilating a pupil of an eye by application of a substantially uniform expansile force around the circumference of the pupil, while precluding focal stress points that may damage the iris. The pupil dilation system disclosed herein comprises a non-bulky, easy to use pupil dilator and a cannular injection device. The pupil dilator disclosed herein is compact, flexible, and remains stable at a pupillary margin of a pupil of an eye during eye surgery. The pupil dilator disclosed herein has a configuration that retains the original shape of the pupil and precludes damage to the iris and the pupil during pupil dilation. The pupil dilator disclosed herein is made of a biocompatible, bioabsorbable material that can be retained in the eye after eye surgery. Natural degradation of the biocompatible, bioabsorbable material of the pupil dilator in the eye avoids complications from surgical manipulation when removing the pupil dilator from the eye.

The pupil dilator disclosed herein comprises a generally circular deformable ring member, herein referred to as a "ring member", made of a flexible material, which permits the ring member to be folded or straightened. The folded form of the ring member has a compacted configuration that can be readily inserted through a small incision in the eye with a surgical manipulating element, for example, folding forceps. The ring member is constructed, for example, from a thermoplastic material or a silicone material. The ring member can also be constructed, for example, from one or more biocompatible materials, bioabsorbable materials, a dissolvable material, a resilient material, a pliable material, and a non-absorbent material. In an embodiment, the ring member can be constructed from a carbohydrate based material, for example, glycan, a disaccharide, a glycosamino-glycan polymer, etc. For example, the ring member is constructed from a carbohydrate based material such as hydroxypropyl cellulose. In another example, the ring member is constructed from a disaccharide such as n-acetyl-glucosamine. In another embodiment, the ring member can also be constructed from a protein based absorbable material. In another embodiment, the ring member is constructed from a synthetic polymer selected from a group comprising, for example, polyglactin, poliglecaprone, polydioxanone, polyacrylamide, polymethacrylate, polyethelene glycol, polyhydroxyalkanoate, polysuccinimide, polyalkene oxide, polygeline, etc. The ring member disclosed herein is adapted to naturally dissolve in a fluid of the eye.

The circumference of the ring member is, for example, from about 3 millimeters to about 16 millimeters. The ring member comprises opposing ends that define an expandable space therebetween. The opposing ends of the ring member are configured to allow the ring member to be flexibly manipulated around the pupillary margin. In an embodiment, one or both the opposing ends of the ring member are of a bulbous configuration. The bulbous configuration of one or both of the opposing ends of the ring member is configured to accommodate one or more connector members of a generally large size. The bulbous configuration of one or both of the opposing ends of the ring member enables controlled movement and manipulation of the ring member around the pupillary margin.

The ring member is configured in an uncoiled configuration to allow insertion of the ring member through a single incision in the eye. The ring member is also configured to unfold from the uncoiled configuration into a generally coiled configuration that conforms to a pupillary aperture of the pupil for engaging the pupillary margin. The ring member is configured to expand circumferentially for application of an expansile force substantially uniformly around the pupillary margin for dilating the pupil along an entirety of a circumference of the ring member.

A circumferential groove is defined on an outer surface of the ring member. The circumferential groove is configured to be in continuous contact with the pupillary margin along the circumference of the ring member, thereby precluding focal points that distort the pupil and stretch the iris. The circumferential groove is configured in one of multiple shapes, for example, a V shape, a U shape, a square shape, etc. In an embodiment, the pupil dilator further comprises one or more transverse ribs configured from the base of the circumferential groove on the outer surface of the ring member. The transverse ribs are configured to frictionally contact the pupillary margin to stabilize the ring member against the pupillary margin.

One or more connector members are positioned at one or more predetermined locations on the circumference of the ring member and/or on one or both of the opposing ends of the ring member. In an embodiment, the connector members are eyelets positioned at predetermined locations along the circumference of the ring member and/or on one or both of the opposing ends of the ring member. In another embodiment, the connector member is a protuberance extending substantially perpendicularly from one or both of the opposing ends of the ring member. Each of the connector members is configured to engage with a surgical manipulating element that allows movement and manipulation of the ring member around the pupillary margin during insertion of the ring member into the eye. In an embodiment, the surgical manipulating element is a surgical hook connected to the cannular injection device of the pupil dilation system, configured to move and manipulate the ring member around the pupillary margin via one or more of the connector members of the ring member. In another embodiment, the surgical manipulating element is a fork of a predetermined shape, for example, a V shape, connected to the cannular injection device, configured to move and manipulate the ring member around the pupillary margin via one or more of the connector members of the ring member.

The cannular injection device of the pupil dilation system disclosed herein comprises a hollow tube and a plunger rod. The hollow tube of the cannular injection device comprises a tubular delivery channel extending outwardly from a front end of the hollow tube. The tubular delivery channel is configured to accommodate the pupil dilator in an uncoiled configuration prior to insertion of the pupil dilator into an anterior chamber of the eye. The plunger rod of the cannular injection device is axially disposed within the tubular delivery channel of the hollow tube and configured to insert the pupil dilator into the anterior chamber of the eye.

The cannular injection device further comprises a knob positioned on the hollow tube. The knob is operably connected to the plunger rod within the tubular delivery channel of the hollow tube for manually propelling the plunger rod to insert the ring member into the anterior chamber of the eye. The surgical manipulating element is operably coupled to the tip of the plunger rod of the cannular injection device. The surgical manipulating element is configured to engageably connect with one or more of the connector members of the ring member of the pupil dilator for positioning, moving, and manipulating the ring member around the pupillary margin.

Also, disclosed herein is a method for dilating a pupil of an eye. The cannular injection device and the pupil dilator comprising the ring member are provided for dilation of the pupil of the eye. The ring member of the pupil dilator is loaded in an uncoiled configuration into the tubular delivery channel defined within the hollow tube of the cannular injection device. The ring member is then inserted in the uncoiled configuration from the tubular delivery channel into the anterior chamber of the eye through a single incision in the eye, by propelling the plunger rod of the cannular injection device. In an embodiment, a curing agent is employed to convert the ring member from a semi-liquid form at room temperature to a semi-solid form for convenient insertion of the ring member into the eye. The ring member is configured to unfold from the uncoiled configuration into a generally coiled configuration that conforms to the pupillary aperture of the pupil. The ring member in the coiled configuration is disposed within the pupillary aperture. The inserted ring member unfolds into a generally circular configuration. The ring member expands radially outwards to engage the pupillary margin within the circumferential groove of the ring member along the circumference of the ring member. The ring member circumferentially applies an expansile force substantially uniformly around the pupillary margin for dilating the pupil along the entirety of the circumference of the ring member. In an embodiment, the ring member is retained in the eye after dilation of the pupil, thereby allowing the ring member to naturally dissolve in a fluid of the eye.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and components disclosed herein.

FIGS. 9A-9E exemplarily illustrate a method for ejecting and inserting the generally circular deformable ring member into the eye for dilating a pupil of the eye using the pupil dilation system.

DETAILED DESCRIPTION OF THE INVENTION

Figure 1:
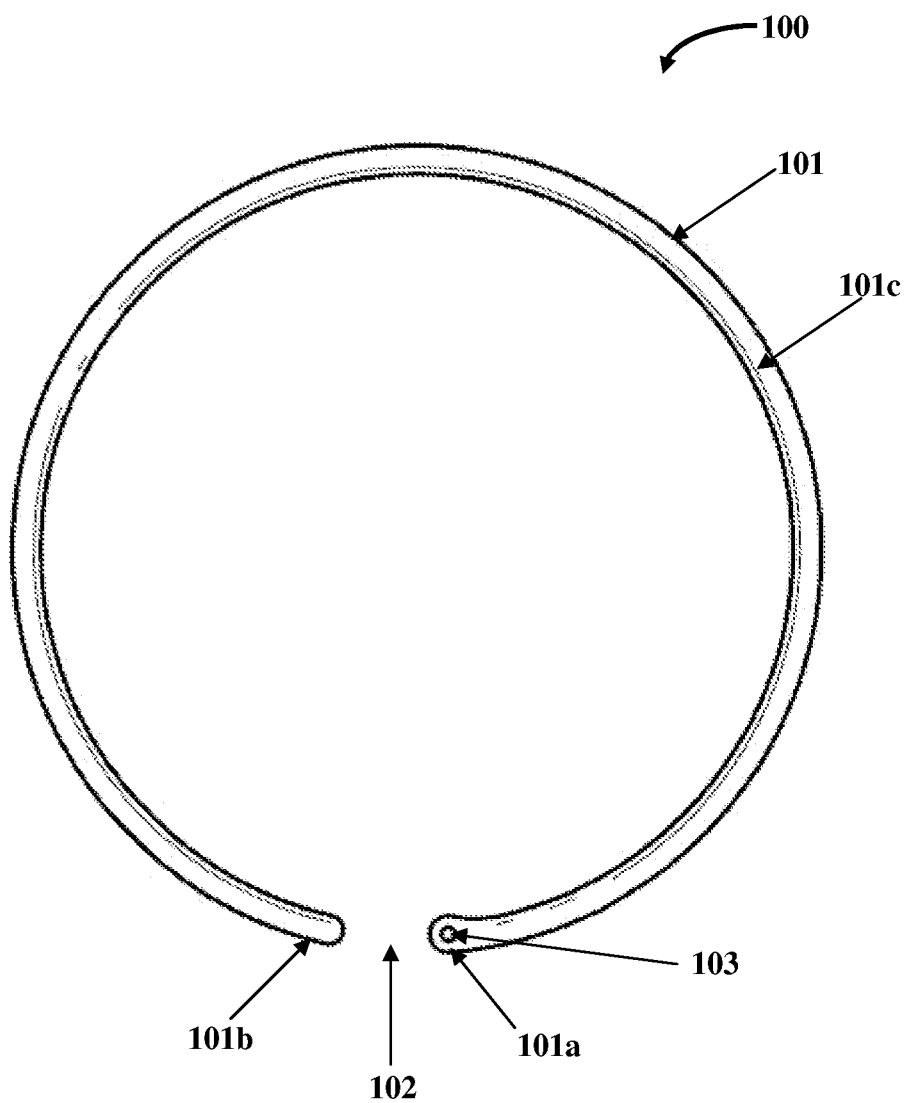
FIG. 1 exemplarily illustrates a top elevation view of a pupil dilator comprising a generally circular deformable ring member, showing a single eyelet positioned at a predetermined location along the circumference of the generally circular deformable ring member.
Figure 2:
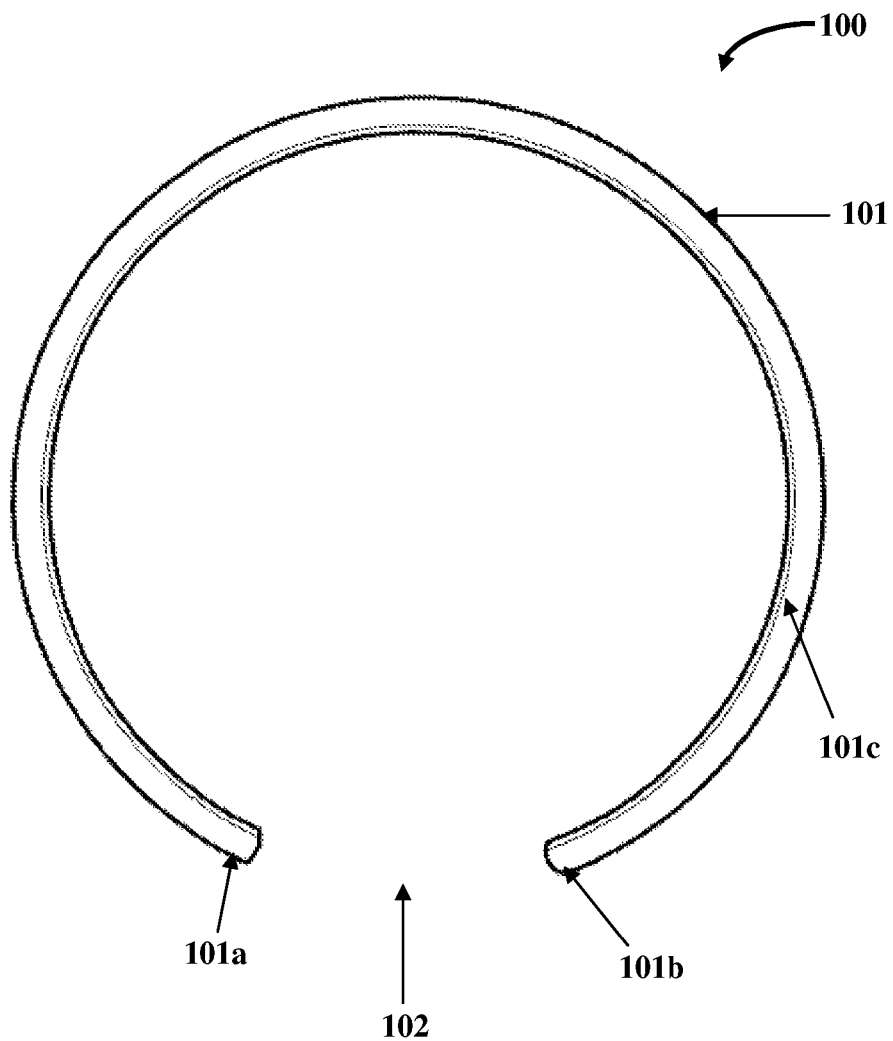
FIG. 2 exemplarily illustrates a bottom view of the pupil dilator.

FIG. 1 and FIG. 2 exemplarily illustrate a top elevation view and a bottom view respectively, of a pupil dilator 100 comprising a generally circular deformable ring member 101. FIG. 1 also shows a single eyelet 103 positioned at a predetermined location along the circumference 101c of the generally circular deformable ring member 101. The generally circular deformable ring member 101 is herein referred to as a "ring member". The ring member 101 is made of a flexible material. In an embodiment, the ring member 101 is constructed from a non-absorbent thermoplastic material, for example, hydroxymethylmethacrylate, silicone, polyamide, polymethylmethacrylate, polyethelene, polyester, polystyrene, polypropylene, polytetrafluorethylene, polyurethane, ethylene-vinyl-acetate, etc., and any combination thereof. The thermoplastic material and the silicone material are configured to have adhesive qualities and configured to be pliable, resilient, and biocompatible. In an embodiment, a curing agent, for example, polydimethylsiloxane or urea-formaldehyde is employed to convert the ring member 101 from a semi-liquid form at room temperature to a semi-solid form. The curing agent may be applied at the time of surgery. The curing agent hardens the biocompatible material of the ring member 101 for convenient insertion of the ring member 101 into the eye 501 as exemplarily illustrated in FIG. 5 and FIGS. 9A-9E. In another embodiment, the ring member 101 is constructed from a dissolvable material or a bioabsorbable material such as a carbohydrate or a protein that is adapted to naturally dissolve in the fluid of the eye 501 exemplarily illustrated in FIG. 5.

The ring member 101 constructed from the bioabsorbable material can be retained in the eye 501 and allowed to naturally dissolve in the fluid of the eye 501. Natural degradation of a bioabsorbable material of the ring member 101 can avoid complications from removal of the ring member 101 from the eye 501. Bioabsorbable materials for construction of the ring member 101 comprise, for example, biocompatible materials such as collagen, or other carbohydrate based materials such as glycan, hydroxypropyl cellulose, a glycosamino-glycan polymer, a disaccharide such as n-acetyl-glucosamine, etc. Examples of other bioabsorbable materials comprise polyglycolic acid, polylactic acid, polyglactin 910 comprising a 9:1 ratio of glycolide per lactide unit, polyglyconate comprising a 9:1 ratio of glycolide per trimethylene carbonate unit, and polydioxanone, a copolymer produced from R-3-hydroxybutyric acid with 4-hydroxybutyric acid, a copolymer produced from R-3-hydroxyoctanoate and R-3-hydroxyhexanoate, a copolymer comprising about 3% to about 8% 4-hydroxybutyric acid polymerized with 3-hydroxybutyric acid, a copolymer of R-3-hydroxyoctanoic acid and R-3-hydroxyhexanoic acid with a Young's modulus value of about 1,000 pounds per square inch (psi) to about 2,000 psi, and a copolymer of R-3-hydroxybutyric acid and 4-hydroxybutyric acid with a Young's modulus ranging from about 3,000 psi to about 22,000 psi, a polymer comprising about 10% R-3-hydroxypentanoic acid and R-3-hydroxybutyric acid, combinations of different hydroxy acid monomers, a hydrogel polymerized from at least one synthetic hydrophilic polyethylene glycol macromer, hydrogels formed from natural polymers such as glycosminoglycans, polysaccharides, proteins, etc., hydrophilic hydrogels, polyacrylamides, polyacrylic acid, polyethylene oxide, starch graft copolymers, acrylate polymer, ester cross-linked polyglucan, etc. In an embodiment, the ring member 101 can also be constructed from a synthetic polymer selected from a group comprising, for example, polyglactin, poliglecaprone, polydioxanone, polyacrylamide, polymethacrylate, polyethelene glycol, polyhydroxyalkanoate, polysuccinimide, polyalkene oxide, polygeline, etc.

The ring member 101 is a flexible discontinuous ring comprising opposing ends 101a and 101b that define an expandable space 102 therebetween as exemplarily illustrated in FIGS. 1-2. The discontinuity of the ring member 101 having an expandable space 102 between the opposing ends 101a and 101b permits the ring member 101 to unfold and expand outwardly in a radial manner. The expandable space 102 permits the ring member 101 to coil into its molded configuration. The opposing ends 101a and 101b of the ring member 101 are configured to allow the ring member 101 to be flexibly manipulated around a pupillary margin 502 of a pupil 503 of an eye 501 exemplarily illustrated in FIG. 5. The ring member 101 is configured to expand or enlarge the pupil 503 to facilitate surgical eye procedures, for example, cataract removal, vitrectomy, retinal repair, etc. The ring member 101 comprises a circumferentially grooved outer surface 101d, as exemplarily illustrated in FIGS. 3A-3B and FIG. 4, that conforms to the pupillary margin 502 of the pupil 503. The circumference 101c of the ring member 101 is, for example, from about 3 millimeters to about 16 millimeters.

Figure 3A:
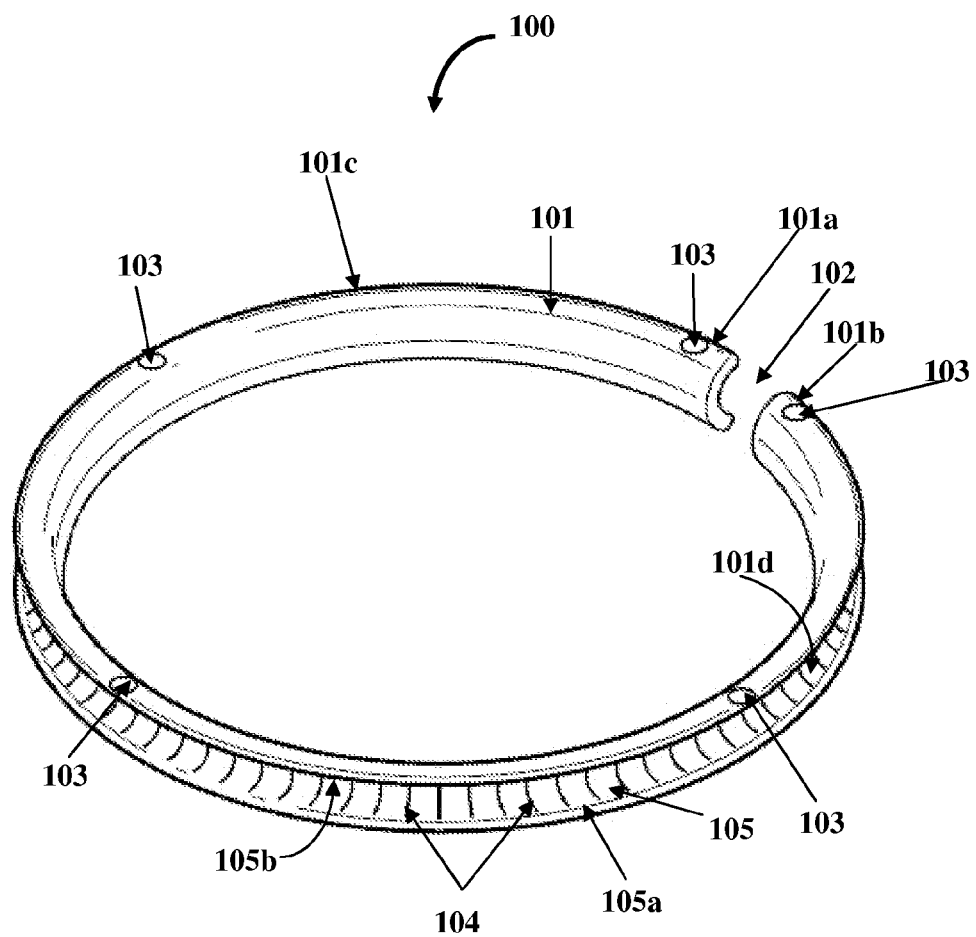
FIG. 3A exemplarily illustrates a perspective view of an embodiment of the generally circular deformable ring member, showing a circumferential groove defined on an outer surface of the generally circular deformable ring member, and multiple eyelets positioned at predetermined locations along the circumference of the generally circular deformable ring member.
Figure 3B:
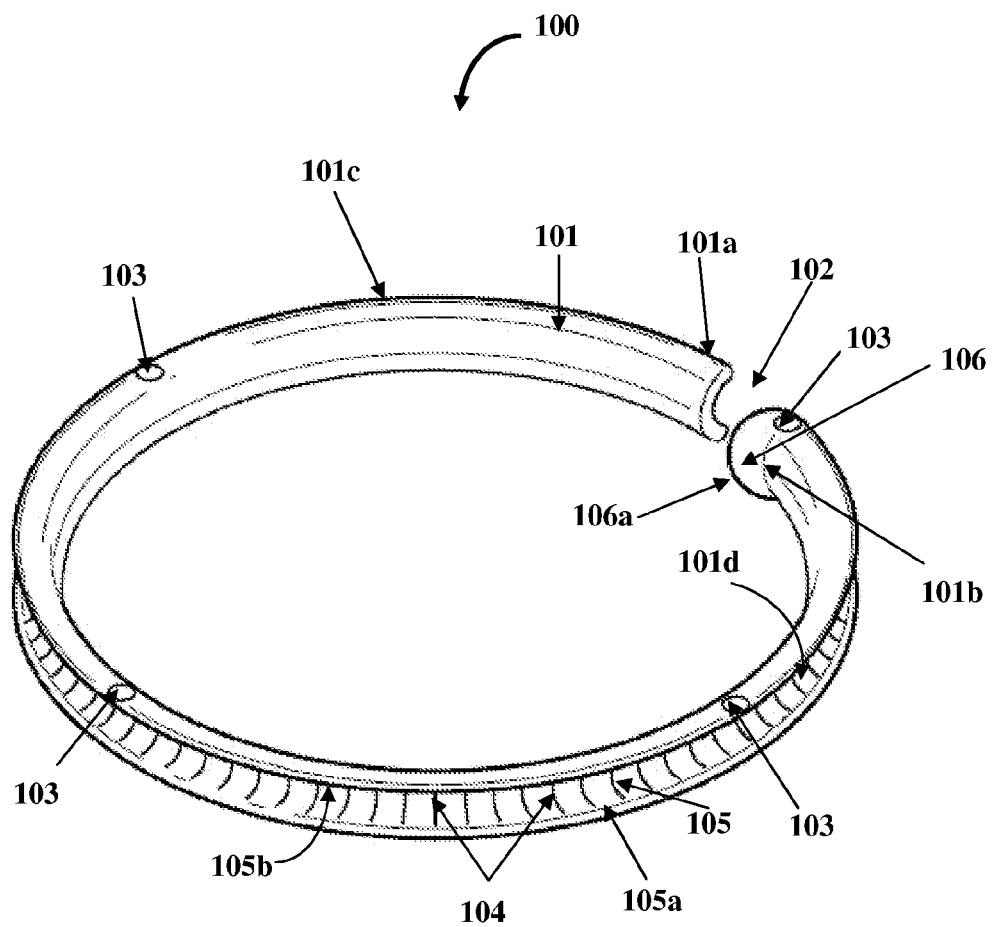
FIG. 3B exemplarily illustrates a perspective view of another embodiment of the generally circular deformable ring member, showing a circumferential groove defined on an outer surface of the generally circular deformable ring member, an opposing end of the generally circular deformable ring member in a bulbous configuration, and multiple eyelets positioned at predetermined locations along the circumference of the generally circular deformable ring member.
Figure 4:
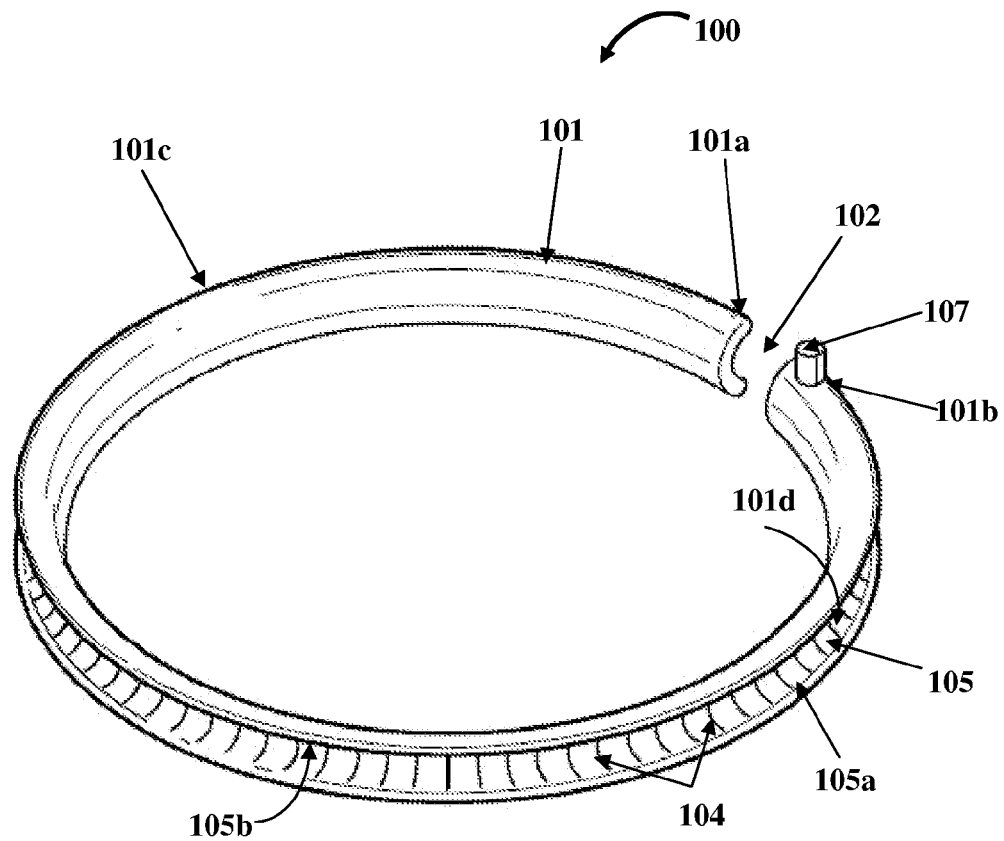
FIG. 4 exemplarily illustrates a perspective view of an embodiment of the generally circular deformable ring member, showing a circumferential groove defined on an outer surface of the generally circular deformable ring member and a protuberance extending substantially perpendicularly from an opposing end of the generally circular deformable ring member.

In an embodiment, one or more connector members, for example, eyelets 103 and/or a protuberance 107 exemplarily illustrated in FIGS. 3A-3B and FIG. 4 respectively, are positioned at one or more predetermined locations on the circumference 101c of the ring member 101 and/or on one or both of the opposing ends 101a and 101b of the ring member 101. Each of the connector members, for example, the eyelets 103 or the protuberance 107 is configured to engage with a surgical manipulating element, for example, a surgical hook 706 exemplarily illustrated in FIGS. 7B-7C, or a fork 707 exemplarily illustrated in FIG. 8, that allows movement and manipulation of the ring member 101 around the pupillary margin 502. The engagement of the connector members, for example, the eyelets 103 and/or the protuberance 107 with the surgical manipulating element, for example, the surgical hook 706 or the fork 707 permits an operator to facilitate positioning of the ring member 101 within the eye 501 while the ring member 101 unfolds to distend the pupil 503. As exemplarily illustrated in FIG. 1, a single eyelet 103 is positioned on an opposing end 101a of the ring member 101.

FIG. 3A exemplarily illustrates a perspective view of an embodiment of the generally circular deformable ring member 101, showing a circumferential groove 105 defined on an outer surface 101d of the ring member 101, and multiple eyelets 103 positioned at predetermined locations along the circumference 101c of the ring member 101. In this embodiment, multiple eyelets 103 are positioned, for example, along the circumference 101c of the ring member 101 and also at the opposing ends 101a and 101b of the ring member 101. The eyelets 103 are configured to engage with a surgical manipulating element, for example, a surgical hook 706 exemplarily illustrated in FIGS. 7B-7C, or a fork 707 exemplarily illustrated in FIG. 8, that allows movement and manipulation of the ring member 101 around the pupillary margin 502 exemplarily illustrated in FIG. 5. Full thickness eyelets 103 of the ring member 101 permit a surgeon to manipulate and position the ring member 101 using the surgical manipulating element, for example, the surgical hook 706 or a lens hook as exemplarily illustrated in FIGS. 7B-7C, or the fork 707 as exemplarily illustrated in FIG. 8, or by using a conventional lens manipulating instrument connected to a cannular injection device 701 exemplarily illustrated in FIGS. 7A-7D. The eyelets 103 are configured as receptacles for the surgical manipulating element, for example, the surgical hook 706 that manipulates and positions the ring member 101 at a desired position within an eye 501 exemplarily illustrated in FIG. 5.

The circumferential groove 105 defined on the outer surface 101d of the ring member 101 is configured to be in continuous contact with the pupillary margin 502 along the circumference 101c of the ring member 101. The circumferential groove 105 of the ring member 101 conforms to and engages the pupillary margin 502 as exemplarily illustrated in FIG. 9C. The circumferential groove 105 of the ring member 101 facilitates proper positioning of the ring member 101 along the pupillary margin 502. The width of the circumferential groove 105 on the outer surface 101d of the ring member 101 is, for example, from about 0.1 millimeters to about 3 millimeters. The depth of the circumferential groove 105 on the outer surface 101d of the ring member 101 is, for example, from about 0.1 millimeters to about 1 millimeter. The circumferential groove 105 is configured in one of multiple shapes. In an embodiment, the circumferential groove 105 is a V-shaped groove. In another embodiment, the circumferential groove 105 is a U-shaped groove. In another embodiment, the circumferential groove 105 is a square base-shaped groove.

In an embodiment, one or more transverse ribs 104 are configured from the base 105a of the circumferential groove 105 that is on the outer surface 101d of the ring member 101. In an embodiment, the transverse ribs 104 extend from the base 105a of the circumferential groove 105 to the lateral edge 105b of the circumferential groove 105. The transverse ribs 104 are thread-like bands configured from the base 105a of the circumferential groove 105. The transverse ribs 104 provide a frictional coefficient when they contact the pupillary margin 502. In an embodiment, the transverse ribs 104 are horizontally arranged at the base 105a of the circumferential groove 105. In this embodiment, the transverse ribs 104 are limited to the base 105a of the circumferential groove 105 and do not extend to the lateral edge 105b of the circumferential groove 105.

As exemplarily illustrated in FIG. 3A, the transverse ribs 104 are spaced apart and form a tread at the base 105a of the circumferential groove 105. The transverse ribs 104 are spaced apart, for example, by a minimum of about 1 millimeter. The number of transverse ribs 104 can range, for example, from about two to multiple transverse ribs 104. The transverse ribs 104 are configured to frictionally contact the pupillary margin 502 to stabilize the ring member 101 against the pupillary margin 502. Each of the transverse ribs 104 is formed of a generally concave arcuate elevation that extends from the base 105a of the circumferential groove 105. The width of each of the transverse ribs 104 is, for example, about 0.05 millimeters. Each of the transverse ribs 104 projects into a concavity of the circumferential groove 105, for example, by about 0.05 millimeters. When the ring member 101 is positioned at the pupillary margin 502, the frictional engagement of the ring member 101 with the pupillary margin 502 provided by multiple transverse ribs 104 stabilizes the position of the ring member 101 against the pupillary margin 502 and limits the rotation of the ring member 101 about the pupillary margin 502.

FIG. 3B exemplarily illustrates a perspective view of another embodiment of the generally circular deformable ring member 101, showing a circumferential groove 105 defined on an outer surface 101d of the ring member 101, an opposing end 101b of the ring member 101 in a bulbous configuration 106, and multiple eyelets 103 positioned at predetermined locations along the circumference 101c of the ring member 101. The eyelets 103 are positioned, for example, along the circumference 101c of the ring member 101 and also at the opposing ends 101a and 101b of the ring member 101 as disclosed in the detailed description of FIG. 3A. The circumferential groove 105 is configured to be in continuous contact with the pupillary margin 502 along the circumference 101c of the ring member 101 as disclosed in the detailed description of FIG. 3A.

In an embodiment, one or more of the opposing ends 101a and 101b of the ring member 101 are of a bulbous configuration 106. The bulbous configuration 106 of one or both of the opposing ends 101a and 101b of the ring member 101 are configured to accommodate one or more of the connector members, for example, the eyelets 103 and/or the protuberance 107 of a generally large size. As exemplarily illustrated in FIG. 3B, the opposing end 101b of the ring member 101 is of a bulbous configuration 106. In an embodiment, both the opposing ends 101a and 101b of the ring member 101 are of a bulbous configuration 106. The bulbous configuration 106 of one or more of the opposing ends 101a and 101b of the ring member 101 enables controlled movement and manipulation of the ring member 101 around the pupillary margin 502. The bulbous configuration 106 of one or more of the opposing ends 101a and 101b of the ring member 101 provides smooth contact surfaces 106a that safely contact the iris 507 and the pupil 503 thereby precluding complications arising from conventional sharp-edged pupil expansion devices that may damage the iris 507 and the pupil 503. The smooth contact surfaces 106a of the bulbous configuration 106 of one or more of the opposing ends 101a and 101b of the ring member 101 also preclude excessive post-operative inflammation and an irregular pupil shape typically caused by sharp-edged pupil expansion devices.

Moreover, the bulbous configuration 106 of one or more of the opposing ends 101a and 101b of the ring member 101 permits eyelets 103 of a large size to be configured in the opposing ends 101a and 101b of the ring member 101. The large eyelets 103 in the ring member 101 permit a surgeon to have enhanced control in the placement and positioning of the ring member 101 within the eye 501.

FIG. 4 exemplarily illustrates a perspective view of an embodiment of the generally circular deformable ring member 101, showing a circumferential groove 105 defined on an outer surface 101d of the ring member 101 and a protuberance 107 extending substantially perpendicularly from an opposing end 101b of the ring member 101. The protuberance 107 is a cylindrically shaped post at the opposing end 101b of the ring member 101. The height of the protuberance 107 is, for example, from about 0.5 millimeters to about 3 millimeters. The protuberance 107 is configured to engage with the surgical manipulating element, for example, a fork 707 exemplarily illustrated in FIG. 8, for moving and manipulating the ring member 101 around the pupillary margin 502 during or after dilation of the pupil 503. A surgeon may use the fork 707, exemplarily illustrated in FIG. 8, to engage the protuberance 107 at the opposing end 101b of the ring member 101 for manipulating the ring member 101. In an embodiment, the protuberance 107 is located at both the opposing ends 101a and 101b of the ring member 101. FIG. 4 also exemplarily illustrates the transverse ribs 104 configured from the base 105a of the circumferential groove 105 that is on the outer surface 101d of the ring member 101.

Figure 5:
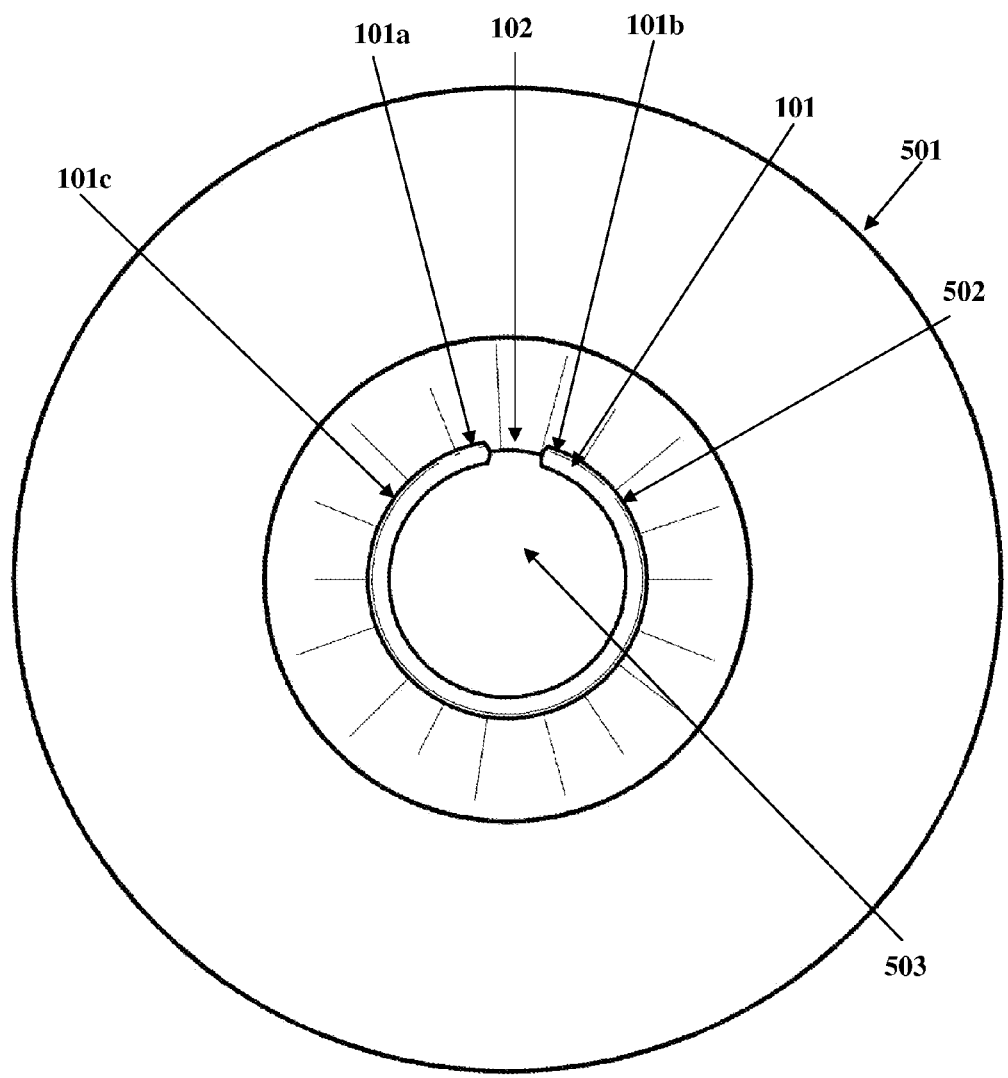
FIG. 5 exemplarily illustrates the generally circular deformable ring member engaged with a pupillary margin of a pupil of an eye.

FIG. 5 exemplarily illustrates the generally circular deformable ring member 101 engaged with a pupillary margin 502 of a pupil 503 of an eye 501. The ring member 101 is configured to expand circumferentially for application of an expansile force substantially uniformly around the pupillary margin 502 for dilating the pupil 503 along the entirety of the circumference 101c of the ring member 101. The ring member 101 expands the diameter of an undilated pupil 503, for example, from about 3 millimeters to about 7 millimeters. The ring member 101 is inserted around the pupillary margin 502 as disclosed in the detailed description of FIGS. 9A-9E and FIG. 10.

Figure 6:
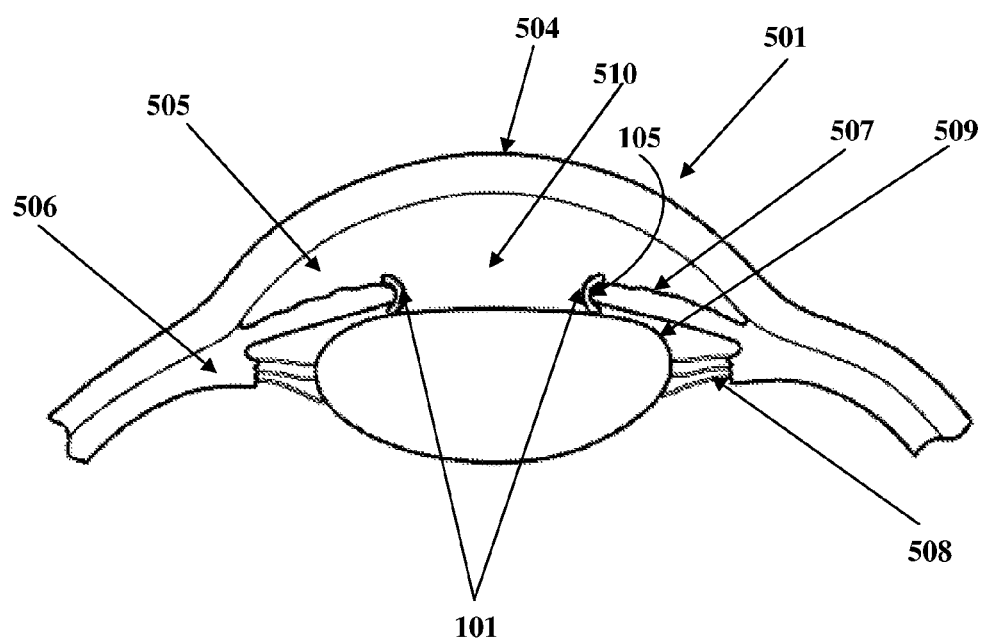
FIG. 6 exemplarily illustrates a view showing the position of the generally circular deformable ring member within an eye.

FIG. 6 exemplarily illustrates a view showing the position of the ring member 101 within an eye 501. FIG. 6 shows the cornea 504, the anterior chamber 505, a pupillary aperture 510, an iris 507, a ciliary body 506, zonules 508, and the lens 509 of the eye 501. Light enters through the pupil 503 shown in FIG. 5, and reaches retinal cells in the back of the eye 501 for vision to occur. The circular sphincter muscle present around the pupil 503 causes the pupil 503 to constrict. The ring member 101 is inserted into the anterior chamber 505 of the eye 501 through a single incision in the cornea 504 of the eye 501 to allow the ring member 101 to engage the pupillary margin 502. The deformable ring member 101 unfolds and enlarges into a coiled configuration. The ring member 101 in the coiled configuration is disposed within the pupillary aperture 510. The iris 507 fits into the circumferential groove 105 of the ring member 101. As the deformable ring member 101 enlarges, the deformable ring member 101 expands the opening of the pupil 503.

FIGS. 7A-7D exemplarily illustrate perspective views of a cannular injection device 701 of a pupil dilation system 700, showing ejection of the generally circular deformable ring member 101 in an uncoiled configuration from a tubular delivery channel 703 of the cannular injection device 701. The pupil dilation system 700 disclosed herein comprises the cannular injection device 701 having a hollow tube 702 and a plunger rod 704 as exemplarily illustrated in FIG. 7A. The hollow tube 702 comprises a tubular delivery channel 703 extending outwardly from a front end 702a of the hollow tube 702. The tubular delivery channel 703 is configured to accommodate the pupil dilator 100 in an uncoiled configuration prior to insertion of the pupil dilator 100 into an anterior chamber 505 of the eye 501 exemplarily illustrated in FIG. 6. The pupil dilator 100 comprising the ring member 101 is exemplarily illustrated in FIGS. 1-4. The ring member 101 of the pupil dilator 100 is loaded into the tubular delivery channel 703 of the hollow tube 702 of the cannular injection device 701. The ring member 101 assumes an uncoiled configuration within the tubular delivery channel 703 of the cannular injection device 701. The slidable plunger rod 704 is axially disposed within the tubular delivery channel 703 of the hollow tube 702 of the cannular injection device 701. The tubular delivery channel 703 encases the slidable plunger rod 704. The plunger rod 704 moves and slides out of the tubular delivery channel 703 to eject the ring member 101 out of the tubular delivery channel 703 and to insert the ring member 101 into the anterior chamber 505 of the eye 501.

Figure 7A:
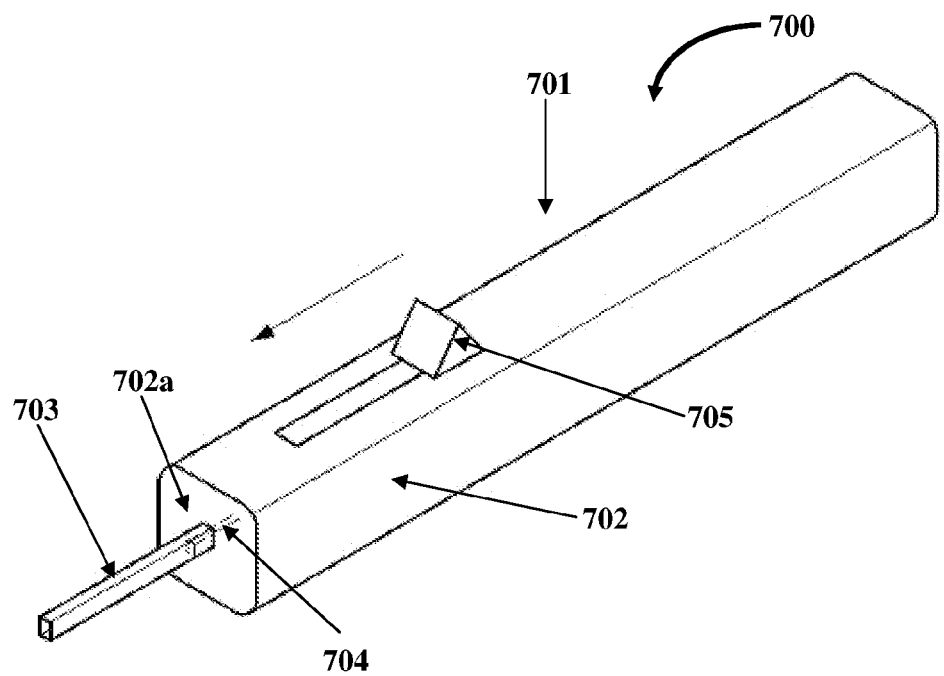
FIGS. 7A-7D exemplarily illustrate perspective views of a cannular injection device of a pupil dilation system, showing ejection of the generally circular deformable ring member in an uncoiled configuration from a tubular delivery channel of the cannular injection device.
Figure 7B:
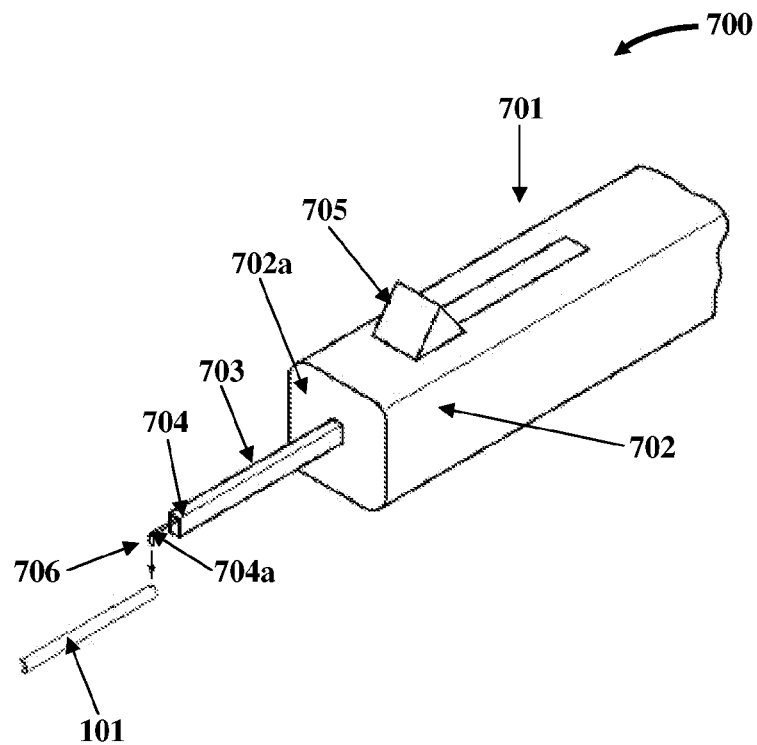
Figure 7C:
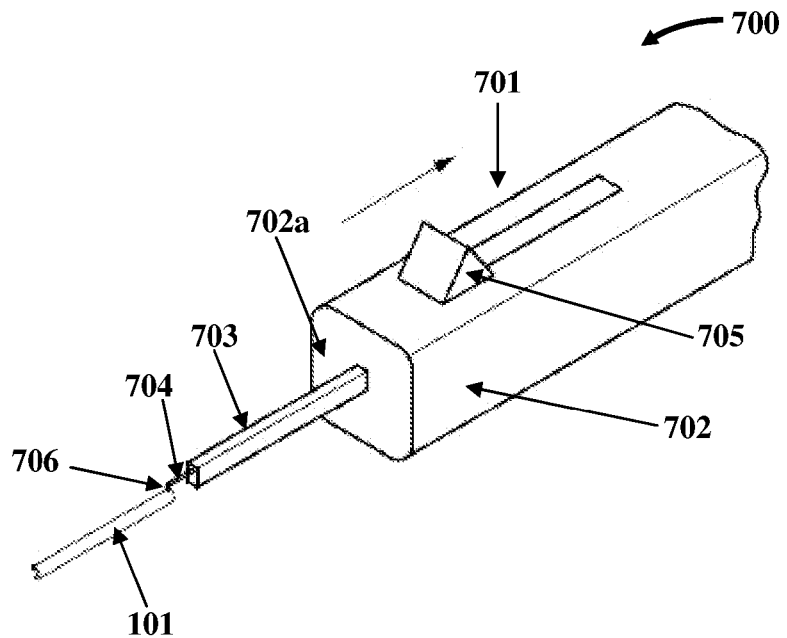
Figure 7D:
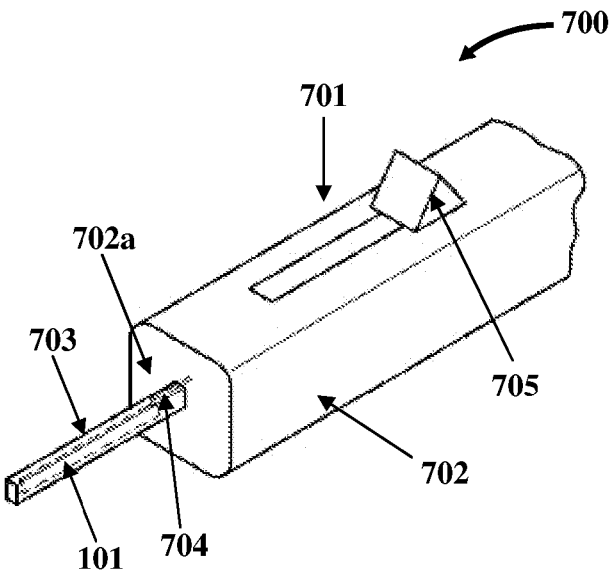

In an embodiment, a surgical manipulating element, for example, a surgical hook 706 exemplarily illustrated in FIGS. 7B-7C, is operably coupled to the tip 704a of the plunger rod 704 for engageably connecting with one or more of the connector members, for example, the eyelets 103 of the ring member 101, exemplarily illustrated in FIG. 1 and FIGS. 3A-3B, for positioning, moving, and manipulating the ring member 101 around the pupillary margin 502. In an embodiment, the surgical manipulating element, for example, the surgical hook 706 extends from the tip 704a of the plunger rod 704. The surgical hook 706 connected to the plunger rod 704 is used for moving and manipulating the ring member 101 around the pupillary margin 502 via the eyelets 103 of the ring member 101. For example, a surgical hook 706 coupled to the plunger rod 704 engages with one of the eyelets 103 of the ring member 101 exemplarily illustrated in FIG. 1 and FIGS. 3A-3B. The surgical hook 706 engaged at one of the eyelets 103 in the ring member 101 positions the ring member 101 to engage the pupillary margin 502.

In an embodiment, the cannular injection device 701 further comprises a knob 705 positioned on the hollow tube 702. The knob 705 is operably connected to the plunger rod 704 within the tubular delivery channel 703 of the hollow tube 702 of the cannular injection device 701. Forward displacement of the knob 705 propels the plunger rod 704 to discharge the ring member 101 as exemplarily illustrated in FIG. 7B, through the tubular delivery channel 703 and insert the ring member 101 into the anterior chamber 505 of the eye 501. The surgical hook 706 engages a connector member, for example, an eyelet 103 of the ring member 101 exemplarily illustrated in FIG. 1 and FIGS. 3A-3B for moving and manipulating the ring member 101 into a desired position around the pupillary margin 502.

The ring member 101 is completely unfolded within the cannular injection device 701. Therefore, the ring member 101 appears coaxial within the tubular delivery channel 703 of the cannular injection device 701. The ring member 101 may be preloaded in the cannular injection device 701 by the manufacturer, or be loaded by a surgeon through the tubular delivery channel 703 of the cannular injection device 701. The surgeon engages the surgical hook 706 to the eyelet 103 and retracts the plunger rod 704 using the knob 705 to pull the ring member 101 into the hollow tube 702 through the tubular delivery channel 703 as exemplarily illustrated in FIGS. 7C-7D. The surgeon uses the reverse maneuver to insert the ring member 101 into the eye 501.

Figure 8:
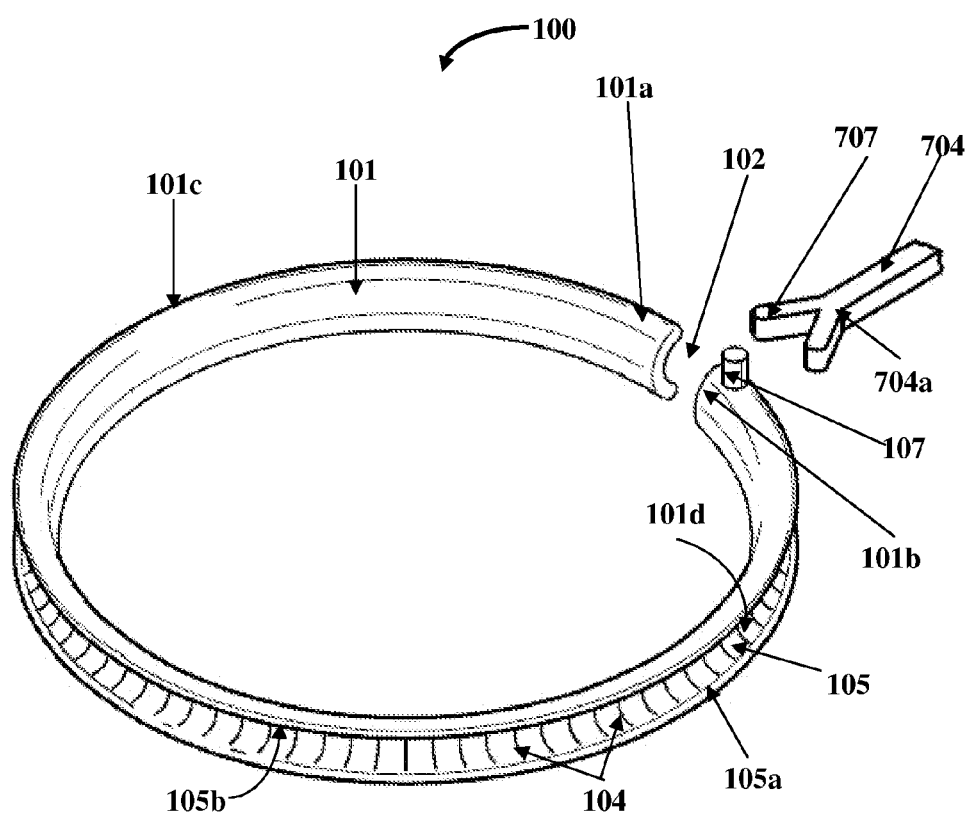
FIG. 8 exemplarily illustrates a surgical manipulating element engageable with a protuberance that extends substantially perpendicularly from an opposing end of the generally circular deformable ring member.

FIG. 8 exemplarily illustrates a surgical manipulating element, for example, a fork 707 engageable with a protuberance 107 that extends substantially perpendicularly from an opposing end 101b of the ring member 101. In an embodiment as exemplarily illustrated in FIG. 8, the surgical manipulating element is a fork 707 of a predetermined shape, for example, a V-shape, operably coupled to the tip 704a of the plunger rod 704 of the cannular injection device 701, exemplarily illustrated in FIG. 7, for moving and manipulating the ring member 101 around the pupillary margin 502, exemplarily illustrated in FIG. 5, via a connector member, for example, the protuberance 107 of the ring member 101. For example, the V-shaped fork 707 exemplarily illustrated in FIG. 8, engages with the protuberance 107 extending substantially perpendicularly from the opposing end 101b of the ring member 101 for moving and manipulating the ring member 101 around the pupillary margin 502.

Figure 9D:
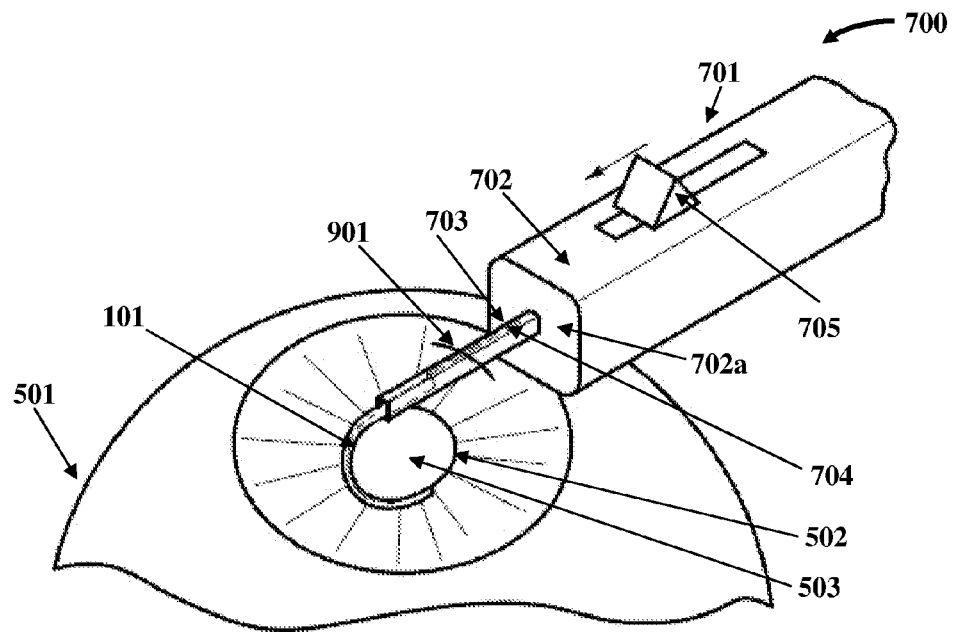
Figure 9E:
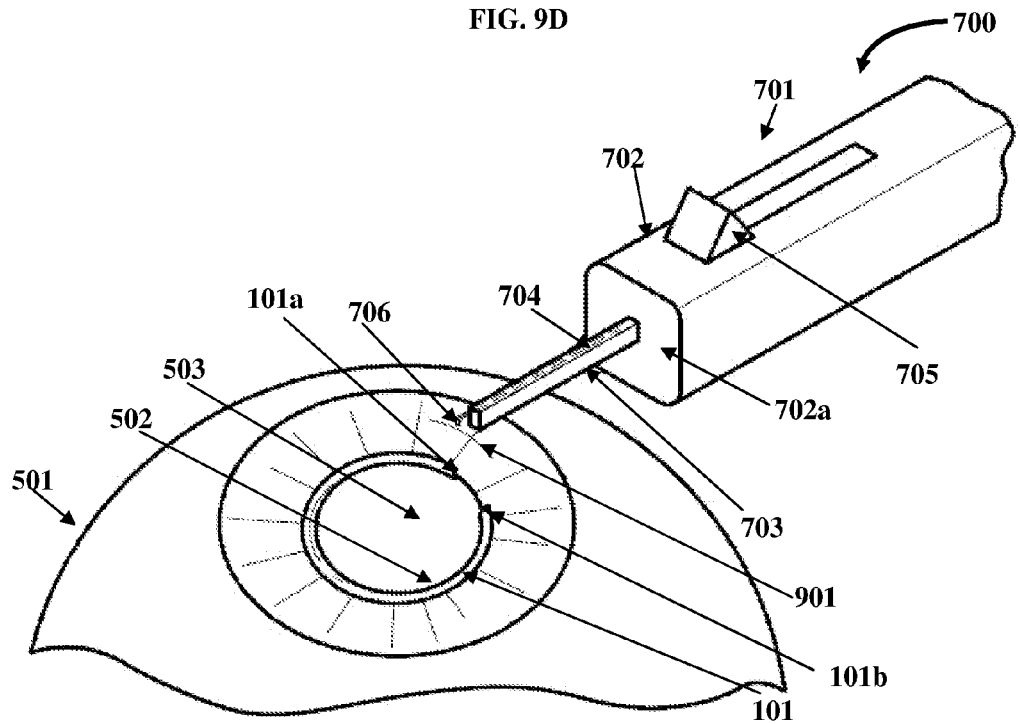

FIGS. 9A-9E exemplarily illustrates a method for ejecting and inserting the generally circular deformable ring member 101 into the eye 501 for dilating a pupil 503 of the eye 501 using the pupil dilation system 700. The ring member 101 is inserted around the pupillary margin 502 of the eye 501 using the cannular injection device 701 as disclosed in the detailed description of FIG. 10. FIG. 9A exemplarily illustrates insertion of the ring member 101 that is loaded into the tubular delivery channel 703 defined within the hollow tube 702 of the cannular injection device 701, in an uncoiled configuration through a single incision 901 in the eye 501. The plunger rod 704 connected to the eyelet 103 of the ring member 101 exemplarily illustrated in FIGS. 3A-3B, is propelled by displacing the knob 705 of the cannular injection device 701 to discharge the ring member 101 from the tubular delivery channel 703 and unfold the ring member 101 from the uncoiled configuration to the coiled configuration as exemplarily illustrated in FIGS. 9B-9C. As the ring member 101 is discharged into the anterior chamber 505 of the eye 501, the ring member 101 changes from the uncoiled configuration to assume its natural coiled configuration. As the ring member 101 becomes coiled, the surgeon manipulates the ring member 101 so that the ring member 101 expands to its prefabricated state and distends or opens the pupil 503. The ring member 101 expands and captures the pupillary margin 502 of the pupil 503 along the circumference 101c of the ring member 101 as exemplarily illustrated in FIGS. 9C-9E.

Figure 10:
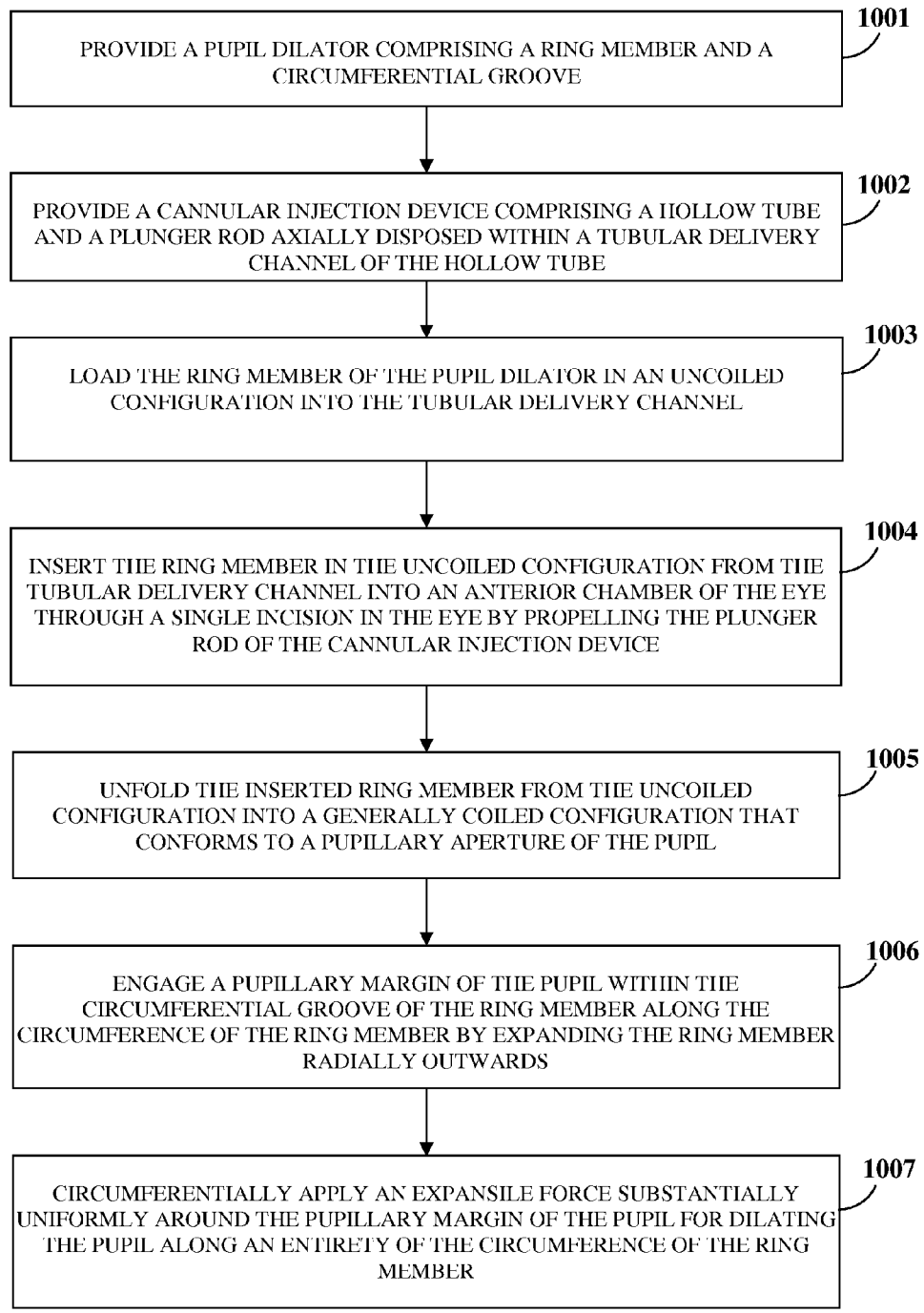
FIG. 10 illustrates a method for mechanically dilating a pupil of an eye.

FIG. 10 illustrates a method for mechanically dilating a pupil 503 of an eye 501 shown in FIGS. 9A-9E. A pupil dilator 100 comprising a generally circular deformable ring member 101 made of a flexible material with opposing ends 101a and 101b that define an expandable space 102 therebetween, and a circumferential groove 105 defined on the outer surface 101d of the ring member 101, as exemplarily illustrated and disclosed in the detailed description of FIGS. 1-4, is provided 1001. Furthermore, a cannular injection device 701 comprising a hollow tube 702 and a plunger rod 704 as disclosed in the detailed description of FIGS. 7A-7D is also provided 1002. The pupil dilator 100 and the cannular injection device 701 constitute the pupil dilation system 700. An operator or a manufacturer of the ring member 101 of the pupil dilator 100 loads 1003 the ring member 101 in an uncoiled configuration into the tubular delivery channel 703 of the hollow tube 702 of the cannular injection device 701, for example, through the forefront of the cannular injection device 701. The ring member 101 in the uncoiled configuration is stretched vertically within the tubular delivery channel 703 of the hollow tube 702.

The operator ejects the ring member 101 from the tubular delivery channel 703 and inserts 1004 the ring member 101 in the uncoiled configuration into the anterior chamber 505 of the eye 501 through a single incision 901 in the cornea 504 of the eye 501 as exemplarily illustrated in FIG. 9A, by displacing the knob 705 and propelling the plunger rod 704 of the cannular injection device 701. As the ring member 101 is injected into the eye 501, the ring member 101 becomes coiled. That is, the ring member 101 unfolds 1005 from the uncoiled configuration into a generally coiled configuration that conforms to the round pupillary aperture 510 of the pupil 503 exemplarily illustrated in FIG. 6. When the ring member 101 is completely coiled, the ring member 101 is circular in configuration. As the ring member 101 coils, the ring member 101 resumes its generally circular configuration, conforms to the shape of the pupil 503, and expands the pupil 503.

The tubular delivery channel 703 proximally extending from the front end 702a of the hollow tube 702 alone enters the cornea 504 of the eye 501 through a single incision 901 as exemplarily illustrated in FIGS. 9A-9D. The body of the cannular injection device 701 remains outside the incision 901. The operator propels the ring member 101 out of the cannular injection device 701 by operating the plunger rod 704. The propelling of the ring member 101 is controlled by the knob 705 operably connected to the plunger rod 704. The operator angles one of the opposing ends 101a and 101b of the ring member 101 to engage one of the edges of the pupillary margin 502. The ring member 101 expands to resume its unstressed generally circular shape, opening the pupillary aperture 510 to a size corresponding to the internal diameter of the ring member 101. The internal diameter of the ring member 101 is, for example, from about 5 millimeters to about 8 millimeters.

In an embodiment, the ring member 101 is introduced into the eye 501 without the cannular injection device 701. The ring member 101 is folded using a surgical hook 706 exemplarily illustrated in FIGS. 7B-7C, or a fork 707 exemplarily illustrated in FIG. 8, or surgical forceps prior to insertion of the ring member 101 through a small surgical incision 901 in the eye 501. As the ring member 101 unfolds in the anterior chamber 505 of the eye 501, the ring member 101 is positioned in the eye 501 using the surgical hook 706, or the fork 707, or forceps via the connector member, for example, the eyelet 103 or the protuberance 107 exemplarily illustrated in FIGS. 3A-3B and FIG. 4 respectively. The deformation of the ring member 101 is performed by flexing the ring member 101 using the surgical hook 706 or the fork 707 engaged at a connector member, for example, the eyelet 103 or the protuberance 107 of the ring member 101. The surgical hook 706 or the fork 707 can point upwards or downwards depending on the orientation of the cannular injection device 701.

The ring member 101 expands radially outwards for engaging 1006 the pupillary margin 502 within the circumferential groove 105 of the ring member 101 along the circumference 101c of the ring member 101. The circumferential groove 105 on the outer surface 101d of the ring member 101 is configured to engage the ring member 101 at the pupillary margin 502 as exemplarily illustrated in FIG. 9C. The transverse ribs 104 at the base 105a of the circumferential groove 105 enable the ring member 101 to frictionally remain in position against the pupillary margin 502. As the operator slowly depresses the plunger rod 704 the opposing portion of the ring member 101 deforms radially outwards to engage the pupillary margin 502.

The ring member 101 circumferentially applies 1007 an expansile force substantially uniformly around the pupillary margin 502 for dilating the pupil 503 along the entirety of the circumference 101c of the ring member 101. The substantially uniform application of the expansile force along the entirety of the circumference 101c of the ring member 101 eliminates tissue retraction at focal points of contact at the pupillary margin 502. The substantially uniform application of the expansile force also eliminates square-shaped pupil dilation, thereby precluding the formation of focal stress points that stretch and distort the iris tissue, and minimizing damage to the pupil 503 and the iris 507. A surgeon may flexibly manipulate the ring member 101 around the pupillary margin 502 via the opposing ends 101a and 101b of the ring member 101. A fully expanded ring member 101 provides expansion of the pupil 503 and facilitates visualization of intraocular structures posterior to the iris plane. Dilation of the pupil 503 permits surgical exposure necessary to remove unwanted tissue, and permits insertion of prosthetic devices such as a lens implant. The method for pupil dilation disclosed herein using the pupil dilation system 700 improves visualization of intraocular structures, facilitates removal of cataracts, and reduces the risk of complications. Circumferentially applying an expansile force substantially uniformly around the pupillary margin 502 in the method disclosed herein allows pupil dilation free from tissue retraction at multiple focal points of contact at the pupillary margin 502.

At the conclusion of surgery, the operator disengages the ring member 101 from the pupil 503, for example, by a standard retractable injector or by the use of a surgical hook 706 or a fork 707 that engages one or more of the connector members, for example, the eyelets 103 and/or the protuberance 107 and withdraws the ring member 101 through the incision 901 in the eye 501. In an embodiment, the operator engages the eyelet 103 with a surgical hook 706 to deform the ring member 101 and disengage the ring member 101 from the pupillary margin 502. The operator then retracts the ring member 101 through the incision 901 and withdraws the ring member 101 from the eye 501.

In another embodiment, the cannular injection device 701, exemplarily illustrated in FIGS. 7A-7D, is deployed to withdraw the ring member 101 from the eye 501. This embodiment requires the operator to extend the retractable plunger rod 704 of the cannular injection device 701. The surgical hook 706 at the tip 104a of the plunger rod 704 engages an eyelet 103 in the ring member 101. After engaging the eyelet 103 with the surgical hook 706, the operator retracts the flexible ring member 101 into the tubular delivery channel 703 of the cannular injection device 701. The cannular injection device 701 is then withdrawn from the eye 501. In an embodiment, the ring member 101 is retained in the eye 501 after the dilation of the pupil 503, thereby allowing the ring member 101 to naturally dissolve in the fluid of the eye 501.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may affect numerous modifications thereto and changes may be made without departing from the scope and spirit of the invention in its aspects.

I claim:

1. A pupil dilator, comprising:
a generally circular deformable ring member made of a flexible material configured to expand circumferentially for application of an expansile force substantially uniformly around a pupillary margin of a pupil of an eye, for dilating said pupil along an entirety of a circumference of said generally circular deformable ring member, said generally circular deformable ring member comprising opposing ends that define an expandable space therebetween;
said generally circular deformable ring member configured in an uncoiled configuration to allow insertion of said generally circular deformable ring member through a single incision in said eye, and configured to unfold from said uncoiled configuration into a generally coiled configuration that conforms to a pupillary aperture of said pupil for engaging said pupillary margin of said pupil;
a circumferential groove defined on an outer surface of said generally circular deformable ring member and configured to be in continuous contact with said pupillary margin of said pupil along said circumference of said generally circular deformable ring member; and
one or more connector members positioned at one or more predetermined locations on one or more of said circumference of said generally circular deformable ring member and said opposing ends of said generally circular deformable ring member, each of said one or more connector members configured to engage with a surgical manipulating element that allows movement and manipulation of said generally circular deformable ring member around said pupillary margin of said pupil.

2. The pupil dilator of claim 1, further comprising one or more transverse ribs configured from a base of said circumferential groove on said outer surface of said generally circular deformable ring member, wherein said one or more transverse ribs are configured to frictionally contact said pupillary margin of said pupil to stabilize said generally circular deformable ring member against said pupillary margin of said pupil.

3. The pupil dilator of claim 1, wherein said one or more connector members are eyelets positioned at said one or more predetermined locations on one or more of said circumference of said generally circular deformable ring member and said opposing ends of said generally circular deformable ring member, wherein said eyelets are configured to engage with said surgical manipulating element for moving and manipulating said generally circular deformable ring member around said pupillary margin of said pupil.

4. The pupil dilator of claim 1, wherein one of said one or more connector members is a protuberance extending substantially perpendicularly from one or more of said opposing ends of said generally circular deformable ring member, wherein said protuberance is configured to engage with said surgical manipulating element for moving and manipulating said generally circular deformable ring member around said pupillary margin of said pupil.

5. The pupil dilator of claim 1, wherein said opposing ends of said generally circular deformable ring member are configured to allow said generally circular deformable ring member to be flexibly manipulated around said pupillary margin of said pupil.

6. The pupil dilator of claim 1, wherein said generally circular deformable ring member is adapted to naturally dissolve in a fluid of said eye.

7. The pupil dilator of claim 1, wherein said surgical manipulating element is a surgical hook connected to a cannular injection device configured to move and manipulate said generally circular deformable ring member around said pupillary margin of said pupil via said one or more connector members of said generally circular deformable ring member.

8. The pupil dilator of claim 1, wherein said surgical manipulating element is a fork of a predetermined shape connected to a cannular injection device configured to move and manipulate said generally circular deformable ring member around said pupillary margin of said pupil via said one or more connector members of said generally circular deformable ring member.

9. The pupil dilator of claim 1, wherein one or more of said opposing ends of said generally circular deformable ring member are of a bulbous configuration configured to accommodate said one or more connector members of a generally large size and to enable controlled said movement and said manipulation of said generally circular deformable ring member around said pupillary margin of said pupil.

10. The pupil dilator of claim 1, wherein said circumferential groove is configured in one of a plurality of shapes, wherein said shapes comprise a V shape, a U shape, and a square shape.

11. The pupil dilator of claim 1, wherein said generally circular deformable ring member is constructed from one of a thermoplastic material and a silicone material.

12. The pupil dilator of claim 1, wherein said generally circular deformable ring member is constructed from a biocompatible and bioabsorbable material.

13. The pupil dilator of claim 1, wherein said generally circular deformable ring member is constructed from a carbohydrate based material, wherein said carbohydrate based material is selected from a group comprising glycan, hydroxypropyl cellulose, a disaccharide, and a glycosamino-glycan polymer.

14. The pupil dilator of claim 1, wherein said generally circular deformable ring member is constructed from a protein based absorbable material.

15. The pupil dilator of claim 1, wherein said generally circular deformable ring member is constructed from a synthetic polymer selected from a group comprising polyglactin, poliglecaprone, polydioxanone, polyacrylamide, polymethacrylate, polyethelene glycol, polyhydroxyalkanoate, polysuccinimide, polyalkene oxide, and polygeline.

16. The pupil dilator of claim 1, wherein said generally circular deformable ring member is constructed from one or more of a biocompatible material, a dissolvable material, a resilient material, a pliable material, and a non-absorbent material.

17. The pupil dilator of claim 1, wherein said circumference of said generally circular deformable ring member is from about 3 millimeters to about 16 millimeters.

18. A pupil dilation system, comprising:
a cannular injection device comprising:
  a hollow tube comprising a tubular delivery channel extending outwardly from a front end of said hollow tube, said tubular delivery channel configured to accommodate a pupil dilator in an uncoiled configuration prior to insertion of said pupil dilator into an anterior chamber of an eye; and
  a plunger rod axially disposed within said tubular delivery channel of said hollow tube and configured to insert said pupil dilator into said anterior chamber of said eye; and
said pupil dilator configured to be inserted into said anterior chamber of said eye using said plunger rod of said cannular injection device, said pupil dilator comprising:
  a generally circular deformable ring member made of a flexible material configured to expand circumferentially for application of an expansile force substantially uniformly around a pupillary margin of a pupil of said eye, for dilating said pupil along an entirety of a circumference of said generally circular deformable ring member, said generally circular deformable ring member comprising opposing ends that define an expandable space therebetween;
  said generally circular deformable ring member configured in said uncoiled configuration to allow insertion of said generally circular deformable ring member through a single incision in said eye, and configured to unfold from said uncoiled configuration into a generally coiled configuration that conforms to a pupillary aperture of said pupil for engaging said pupillary margin of said pupil;
  a circumferential groove defined on an outer surface of said generally circular deformable ring member and configured to be in continuous contact with said pupillary margin of said pupil along said circumference of said generally circular deformable ring member; and
  one or more connector members positioned at one or more predetermined locations on one or more of said circumference of said generally circular deformable ring member and said opposing ends of said generally circular deformable ring member, each of said one or more connector members configured to engage with a surgical manipulating element connected to said cannular injection device that allows movement and manipulation of said generally circular deformable ring member around said pupillary margin of said pupil.

19. The pupil dilation system of claim 18, wherein said pupil dilator further comprises one or more transverse ribs configured from a base of said circumferential groove on said outer surface of said generally circular deformable ring member, wherein said one or more transverse ribs are configured to frictionally contact said pupillary margin of said pupil to stabilize said generally circular deformable ring member against said pupillary margin of said pupil.

20. The pupil dilation system of claim 18, wherein said opposing ends of said generally circular deformable ring member of said pupil dilator are configured to allow said generally circular deformable ring member to be flexibly manipulated around said pupillary margin of said pupil.

21. The pupil dilation system of claim 18, wherein said one or more connector members of said generally circular deformable ring member of said pupil dilator are eyelets positioned at said one or more predetermined locations on one or more of said circumference of said generally circular deformable ring member and said opposing ends of said generally circular deformable ring member, wherein said eyelets are configured to engage with said surgical manipulating element for moving and manipulating said generally circular deformable ring member around said pupillary margin of said pupil.

22. The pupil dilation system of claim 18, wherein one of said one or more connector members of said generally circular deformable ring member of said pupil dilator is a protuberance extending substantially perpendicularly from one or more of said opposing ends of said generally circular deformable ring member, wherein said protuberance is configured to engage with said surgical manipulating element for moving and manipulating said generally circular deformable ring member around said pupillary margin of said pupil.

23. The pupil dilation system of claim 18, wherein said generally circular deformable ring member of said pupil dilator is adapted to naturally dissolve in a fluid of said eye.

24. The pupil dilation system of claim 18, wherein said surgical manipulating element is operably coupled to a tip of said plunger rod of said cannular injection device, wherein said surgical manipulating element is configured to engageably connect with said one or more connector members of said generally circular deformable ring member of said pupil dilator for positioning, moving, and manipulating said generally circular deformable ring member around said pupillary margin of said pupil.

25. The pupil dilation system of claim 18, wherein said cannular injection device further comprises a knob positioned on said hollow tube and operably connected to said plunger rod within said tubular delivery channel of said hollow tube, wherein said knob is configured to manually propel said plunger rod to insert said generally circular deformable ring member of said pupil dilator into said anterior chamber of said eye.

26. The pupil dilation system of claim 18, wherein said surgical manipulating element is a surgical hook operably coupled to a tip of said plunger rod of said cannular injection device, wherein said surgical hook is configured to move and manipulate said generally circular deformable ring member of said pupil dilator around said pupillary margin of said pupil via said one or more connector members of said generally circular deformable ring member.

27. The pupil dilation system of claim 18, wherein said surgical manipulating element is a fork of a predetermined shape operably coupled to a tip of said plunger rod of said cannular injection device, wherein said fork is configured to move and manipulate said generally circular deformable ring member of said pupil dilator around said pupillary margin of said pupil via said one or more connector members of said generally circular deformable ring member.

28. The pupil dilation system of claim 18, wherein one or more of said opposing ends of said generally circular deformable ring member of said pupil dilator are of a bulbous configuration configured to accommodate said one or more connector members of a generally large size and to enable controlled said movement and said manipulation of said generally circular deformable ring member around said pupillary margin of said pupil.

29. The pupil dilation system of claim 18, wherein said generally circular deformable ring member of said pupil dilator is constructed from one of a thermoplastic material, a silicone material, a biocompatible and bioabsorbable material, a dissolvable material, a carbohydrate based absorbable material, a protein based absorbable material, and a synthetic polymer.

30. A method for dilating a pupil of an eye, comprising:
providing a pupil dilator comprising:
a generally circular deformable ring member made of a flexible material, said generally circular deformable ring member comprising opposing ends that define an expandable space therebetween; and
a circumferential groove defined on an outer surface of said generally circular deformable ring member and configured to be in continuous contact with a pupillary margin of said pupil along a circumference of said generally circular deformable ring member;
loading said generally circular deformable ring member of said pupil dilator in an uncoiled configuration into a tubular delivery channel defined within a hollow tube of a cannular injection device;
inserting said generally circular deformable ring member in said uncoiled configuration from said tubular delivery channel into an anterior chamber of said eye through a single incision in said eye, by propelling a plunger rod axially disposed within said tubular delivery channel of said cannular injection device, wherein said generally circular deformable ring member is configured to unfold from said uncoiled configuration into a generally coiled configuration that conforms to a pupillary aperture of said pupil;

engaging said pupillary margin of said pupil with said circumferential groove of said generally circular deformable ring member along said circumference of said generally circular deformable ring member by expanding said generally circular deformable ring member radially outwards; and
circumferentially applying an expansile force substantially uniformly around said pupillary margin of said pupil, for dilating said pupil along an entirety of said circumference of said generally circular deformable ring member;
whereby said circumferential application of said expansile force substantially uniformly around said pupillary margin of said pupil allows said dilation of said pupil free from tissue retraction at multiple focal points of contact at said pupillary margin of said pupil.

31. The method of claim 30, further comprising retaining said generally circular deformable ring member in said eye after said dilation of said pupil, wherein said generally circular deformable ring member is adapted to naturally dissolve in a fluid of said eye.

32. The method of claim 30, wherein said pupil dilator further comprises one or more connector members positioned at one or more predetermined locations on one or more of said circumference of said generally circular deformable ring member and said opposing ends of said generally circular deformable ring member, wherein each of said one or more connector members is configured to engage with a surgical manipulating element connected to said cannular injection device that allows movement and manipulation of said generally circular deformable ring member around said pupillary margin of said pupil.

33. The method of claim 32, wherein said one or more connector members are eyelets positioned at said one or more predetermined locations on one or more of said circumference of said generally circular deformable ring member and said opposing ends of said generally circular deformable ring member.

34. The method of claim 32, wherein one of said one or more connector members is a protuberance extending substantially perpendicularly from one or more of said opposing ends of said generally circular deformable ring member.

35. The method of claim 30, wherein said pupil dilator further comprises one or more transverse ribs configured from a base of said circumferential groove on said outer surface of said generally circular deformable ring member, wherein said one or more transverse ribs are configured to frictionally contact said pupillary margin of said pupil to stabilize said generally circular deformable ring member against said pupillary margin of said pupil.

36. The method of claim 30, further comprising flexibly manipulating said generally circular deformable ring member around said pupillary margin of said pupil via said opposing ends of said generally circular deformable ring member.

37. The method of claim 30, wherein said generally circular deformable ring member of said pupil dilator is constructed from one of a thermoplastic material, a silicone material, a biocompatible and bioabsorbable material, a dissolvable material, a carbohydrate based absorbable material, a protein based absorbable material, and a synthetic polymer.

38. The method of claim 30, further comprising employing a curing agent configured to convert said generally circular deformable ring member from a semi-liquid form at room temperature to a semi-solid form.

39. A method for dilating a pupil of an eye, comprising:
providing a pupil dilator comprising:

a generally circular deformable ring member made of a flexible material, said generally circular deformable ring member comprising opposing ends that define an expandable space therebetween; and a circumferential groove defined on an outer surface of said generally circular deformable ring member and configured to be in continuous contact with a pupillary margin of said pupil along a circumference of said generally circular deformable ring member;

providing a cannular injection device comprising:

a hollow tube comprising a tubular delivery channel extending outwardly from a front end of said hollow tube, said tubular delivery channel configured to accommodate said pupil dilator in an uncoiled configuration prior to insertion of said pupil dilator into an anterior chamber of said eye; and a plunger rod axially disposed within said tubular delivery channel of said hollow tube and configured to insert said pupil dilator into said anterior chamber of said eye;

loading said generally circular deformable ring member of said pupil dilator in an uncoiled configuration into said tubular delivery channel defined within said hollow tube of said cannular injection device;

inserting said generally circular deformable ring member in said uncoiled configuration from said tubular delivery channel into said anterior chamber of said eye through a single incision in said eye, by propelling said plunger rod of said cannular injection device, wherein said generally circular deformable ring member is configured to unfold from said uncoiled configuration into a generally coiled configuration that conforms to a pupillary aperture of said pupil;

engaging said pupillary margin of said pupil within said circumferential groove of said generally circular deformable ring member along said circumference of said generally circular deformable ring member by expanding said generally circular deformable ring member radially outwards; and circumferentially applying an expansile force substantially uniformly around said pupillary margin of said pupil, for dilating said pupil along an entirety of said circumference of said generally circular deformable ring member.

40. The method of claim 39, further comprising retaining said generally circular deformable ring member in said eye after said dilation of said pupil, wherein said generally circular deformable ring member is adapted to naturally dissolve in a fluid of said eye.

41. The method of claim 39, wherein said pupil dilator further comprises one or more connector members positioned at one or more predetermined locations on one or more of said circumference of said generally circular deformable ring member and said opposing ends of said generally circular deformable ring member, wherein said one or more connector members is configured to engage with a surgical manipulating element connected to said cannular injection device that allows movement and manipulation of said generally circular deformable ring member around said pupillary margin of said pupil.

42. The method of claim 39, wherein said generally circular deformable ring member of said pupil dilator is constructed from one of a thermoplastic material, a silicone material, a biocompatible and bioabsorbable material, a dissolvable material, a carbohydrate based absorbable material, a protein based absorbable material, and a synthetic polymer.

43. The method of claim 39, further comprising employing a curing agent configured to convert said generally circular deformable ring member from a semi-liquid form at room temperature to a semi-solid form.

* * * * *